Figure 1:
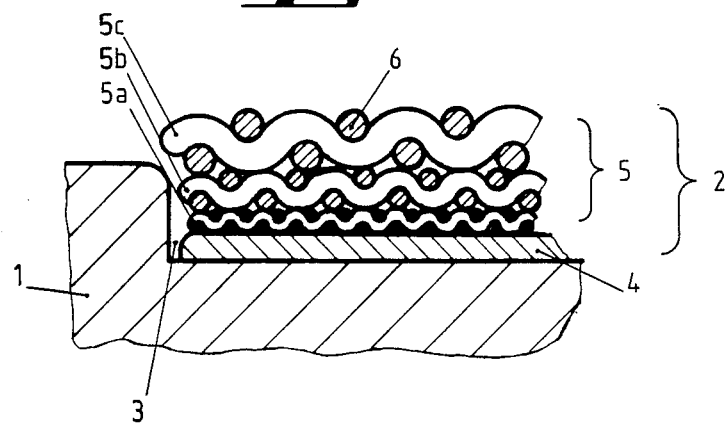

United States Patent [19]

Frey et al.

[11] Patent Number: 4,976,738
[45] Date of Patent: Dec. 11, 1990

[54] POROUS METAL OVERLAY FOR AN IMPLANT SURFACE

[75] Inventors: Otto Frey; Manfred Semlitsch; Heinz Weber, all of Winterthur, Switzerland

[73] Assignee: Sulzer Brothers Limited, Winterthur, Switzerland

[21] Appl. No.: 803,713

[22] Filed: Dec. 2, 1985

[30] Foreign Application Priority Data

Jan. 9, 1985 [CH] Switzerland .......................... 82/85-2

[51] Int. Cl.$^5$ ............................................. A61F 2/28
[52] U.S. Cl. .......................................... 623/16; 623/23
[58] Field of Search ................ 623/23, 16, 20, 66, 623/22, 18; 128/92 R, 92 VV, 92 VW

[56] References Cited

U.S. PATENT DOCUMENTS

| 3,906,550 | 9/1975 | Rostoker et al. ...................... 623/16 |
| 4,064,567 | 12/1977 | Buestein et al. .................. 623/23 X |
| 4,479,271 | 10/1984 | Bolesky et al. .................... 623/18 X |
| 4,536,894 | 8/1985 | Galante et al. .................... 623/16 X |
| 4,542,539 | 9/1985 | Rowe, Jr. et al. ................. 623/10 X |

FOREIGN PATENT DOCUMENTS 0038902 11/1981 European Pat. Off. .............. 623/22

Primary Examiner—Alan W. Cannon
Attorney, Agent, or Firm—Kenyon & Kenyon

[57] ABSTRACT

The porous metal overlay for an implant surface is comprised of a plurality of layers of stacked metal grids. Each layer is provided with pores which are of a size which decrease in the direction of the implant surface steadily, that is, without enlargement in an intermediate layer. The progressively decreasing porous sizes provide for a steady ingrowth and nourishment of the ingrowing tissue.

17 Claims, 1 Drawing Sheet

POROUS METAL OVERLAY FOR AN IMPLANT SURFACE

This invention relates to a porous metal overlay for an implant surface. More particularly, this invention relates to a porous structure for a bone implant.

Heretofore, a number of techniques have been known for making a surface of an implant to be implanted in the human body porous in order to facilitate or permit in growth of tissue. For example, German A.S. No. 2404214 describes arrangements in which one or more layers of similar metal grids, preferably made of expanded metal, are connected, preferably welded, to the core of an implant body. These metal grids have been identical for all layers and have been formed of wire mesh so that their "pores", as formed by the grid openings, overlap at least partially when the individual layers are stacked in order to produce open pores which pass through the layers. In this known structure, a minimum size of 0.05 millimeters is specified for the pores. However, in these constructions, the pore size is the same from layer-to-layer because of the constant mesh clearances. Thus, the pores of the inner layers which are situated towards the implant core may not be completely filled with tissue or, if filled, that the "inner tissue" is not sufficiently nourished so that this tissue necrotizes.

Porous structures have also been known, for example from German 0.S. No. 3036520 wherein an implant core is covered with one or more layers of wire nets of equal mesh clearance with the layers stacked directly or in an offset manner. However, the same problems arise in these structures.

Accordingly, it is an object of the invention to provide an effective porous surface for an implant for the ingrowth of tissue.

It is another object of the invention to provide a porous metal overlay for an implant surface into which tissue may grow and be nourished in a reliable manner.

Briefly, the invention provides a porous metal overlay for an implant surface which is comprised of a plurality of layers of stacked metal grids. In accordance with the invention, each layer has a plurality of pores with the size of the pores being of decreasing size in a direction from the outer surface of the overlay to an opposite inner surface. The overlay is such that a continuous and defined decrease of pore size is ensured at the transition from the outer layers to the inner layers without interruption by expansion of the pore sizes.

By controlling the reduction of the pore size from layer to layer, the ramification of the ingrowing tissue is steady, i.e. that is the ingrowing tissue ramifies without interruption by an enlargement of the pores in an intermediate layer. In addition, the controlled reduction of the pore size provides for even finer dendrites so that nourishment of the fine ends of the resulting trabeculae is ensured.

The individual layers of the overlay may be stacked in an offset manner and/or turned around an axis normal to the surface of the layers relative to each other. Further, the overlay layers may be formed as grids or as fabrics and braids. Any suitable known material which is useful for a metal implant may be used and preferrably, titanium or titanium alloys which are regarded as especially tissue-friendly.

In order to reduce the thermal loads on an implant shank which might lead to undesirable structure variations and, thus, to inferior mechanical properties, such as strength or toughness during the securement of the porous overlay, as by welding or sintering, the layers may be applied via an intermediate plate. In this embodiment, the layers of the overlay are firmly connected to a plate, for example by sintering (diffusion welding) and the plate is, in turn, secured to the anchoring shank of the implant, for example by individual spot welds or may be connected with the shank by a mechanical connection such as screws. Another advantage of the plate is that, being generally made of an especially tissue-friendly material, the plate isolates the accreting tissue from the shank of the implant which may be made of less tissue-friendly material. Furthermore, the plate forms a well defined limit up to which the tissue may grow in.

In order to increase the contact surface for the ingrowing tissue, especially when using wire nets or to smooth the individual layers, the stacked layers of the metal grids may be rolled as a whole or, at least, the grids of individual layers may be rolled before stacking.

Experimentally, it has been found to be especially suitable for the porous structures if the mesh clearances and/or the bar widths of the grid have an absolute value between 0.05 and 1.5 millimeters and/or if the pore volumes in the individual layers is from 20% to 90%.

Figure 2:
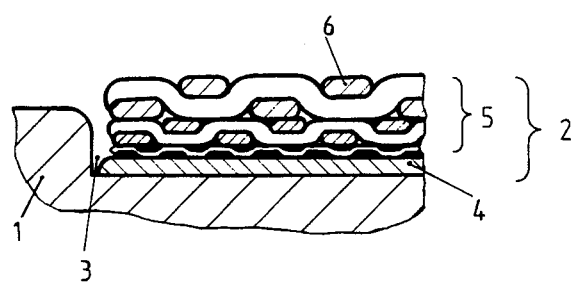

These and other objects and advantages of the invention will become more apparent from the following detailed description taken in conjunction with the accompanying drawings wherein:

FIG. 1 illustrates a cross sectional view of an overlay according to the invention applied on an anchoring shank of a prosthesis; and FIG. 2 illustrates a modified embodiment of an overlay in accordance with the invention.

Referring to FIG. 1, the anchoring shank 1, for example of a metal implant for use as a hip joint endoprosthesis is provided with an overlay 2 formed of a tissue-friendly surface structure and into which bone tissue may grow in the course of time for the anchoring of the shank 1 in a bone without the need for cement. As indicated, the overlay 2 may lie within a depression 3 of the shank 1.

The overlay 2 is formed of a metal plate 4 and of three layers of wire mesh 5. The plate 4 is secured to the shank 1 in any suitable manner, for example, by spot welds or by mechanical means such as screws (not shown).

Each layer 5 is made of a metal grid of wires 6 so as to form pores and bars. In addition, the size of the pores are of decreasing size in a direction from the outermost layer 5c remote from the shank 1 to the innermost layer 5a adjacent to the shank 1. In addition, the diameters of the wires 6 also decrease in the direction towards the shank 1 from the outermost layer 5c to the innermost layer 5a. Thus, the pore size decreases steadily from outside to the inside with each layer having a uniform porosity. For example, the innermost layer 5a has wires 6 of a diameter of 0.1 millimeter with a mesh clearance of 0.2 millimeters; the middle layer 5b is formed of wires of a diameter of 0.25 millimeters with a mesh clearance of 0.5 millimeters and the remote layer 5c is made of wires of a diameter of 0.5 millimeters and a mesh clearance of 1.0 millimeters.

The overlay 2 is formed of one of the metals known to be especially tissue-friendly, such as titanium, tantalum, niobium, zirconium or alloys having one of these metals as a base material.

In the process of production, the individual layers 5a, 5b, 5c of the overlay 2 are first fitted together separately from the plate 4. During this time, a metallurgical bond may be formed between the individual layers 5a, 5b, 5c. Thereafter, the layers 5a, 5b, 5c are joined to the plate 4, for example, by sintering or welding. However, other methods are also possible, such as gluing or bonding. Alternatively, the individual layers 5a, 5b, 5c and plate 4 may be secured together in one operation.

After formation of the overlay 2, the entire overlay is secured on the implant shank 1 at a number of points, preferrably by spot welding.

Referring to FIG. 2 wherein like reference characters indicate like parts as above, the individual layers 5 of the overlay 2 may be deformed by rolling before fabrication of the overlay 2. The deformation by rolling not only permits an increase in the surface of the wire 6 at which bone tissue is to accrete while the wire diameter remains the same, but also reduces the thickness of the overlay 2.

The invention thus provides a porous metal overlay which can be secured to an anchoring shank of a prosthesis in a relatively simple manner while providing a porous structure into which tissue may grow in a reliable manner.

Further, the invention provides a porous structure into which tissue may grow in a steady ramified manner while producing ever finer dendrites which can be nourished without necrosis occurring.

Further, the invention provides for an optimum in growth and accretion of bone tissue into the surface of an implant in a reliable efficient manner.

What is claimed is:

1. A porous metal overlay for an implant surface comprising a plurality of layers of stacked metal grids having a controlled reduction of pore size from an outer surface to an opposite inner surface, each said layer having a plurality of pores therein with the size of said pores being of decreasing size in a direction form said outer surface of said overlay to said opposite inner surface.

2. A porous metal overlay as set forth in claim 1 which further comprises a plate secured to said layer at said opposite inner surface.

3. A porous metal overlay as set forth in claim 1 wherein at least some of said layers are characterized in having been rolled prior to stacking.

4. A porous metal overlay as set forth in claim 1 wherein each layer has pores and bar widths in a range of from 0.05 millimeters to 1.5 millimeters.

5. A porous metal overlay as set forth in claim 1 wherein each layer has a pore volume of from 20% to 90%.

6. A porous structure for a bone implant comprising a plurality of stacked layers of metal grids, each layer having a uniform porosity with a plurality of pores therein, said layers having a controlled reduction of pore size with the pore size of each layer decreasing in size from one surface of the structure to an opposite surface of the structure.

7. A porous structure as set forth in claim 6 wherein each layer is formed of a material selected from the group consisting of titanium, tantalum, niobium, zirconium and alloys thereof.

8. A porous structure as set forth in claim 6 wherein each layer has pores and bar widths in a range of from 0.05 millimeters to 1.5 millimeters.

9. A porous structure as set forth in claim 6 wherein each layer has a pore volume of from 20% to 90%.

10. A porous structure as set forth in claim 6 which further comprises a plate secured to said opposite surface.

11. A porous structure as set forth in claim 10 wherein each said layer and said plate is formed of a material selected from the group consisting of titanium, tantalum, niobium, zirconium and alloys thereof.

12. In combination
an anchoring shank for a prosthesis; and
a plurality of layers of metal grids secured to said shank for an accretion of tissue therein, each layer having a plurality of pores therein with the pore size of each layer decreasing in size from a layer remote from said shank to a layer adjacent said shank to provide a controlled reduction of pore size from said remote layer to said layer adjacent said shank whereby ingrowing tissue is able to ramify without interruption by an enlargement of said pores in an intermediate layer.

13. The combination as set forth in claim 12 wherein said pores of said layers are of a size of from 0.05 millimeters to 1.5 millimeters.

14. The combination as set forth in claim 12 which further comprises a metal plate secured to and between said shank and said layer adjacent said shank.

15. The combination as set forth in claim 14 wherein said plate and each said layer is formed of a material selected group consisting of titanunim, tantalum, niobium, zirconium and alloys thereof.

16. The combination as set forth in claim 15 wherein said pores of each layer are of a size of from 0.05 millimeters to 1.5 millimeters and each layer has a pore volume of from 20% to 90%.

17. The combination as set forth in claim 15 wherein said layers total three and wherein said layer adjacent said shank is made of wires of a diameter of 0.1 millimeters with a mesh clearance of 0.20 millimeters, the middle layer is made of wires of a diameter of 0.25 millimeters with a mesh clearance of 0.50 millimeters and the remote layer is made of wires of a diameter of 0.5 millimeters and a mesh clearance of 1.0 millimeters.

* * * * *

UNITED STATES PATENT AND TRADEMARK OFFICE
CERTIFICATE OF CORRECTION

PATENT NO. : 4,976,738

DATED : December 11, 1990

INVENTOR(S) : OTTO FREY, et al

It is certified that error appears in the above-identified patent and that said Letters Patent is hereby corrected as shown below:

Column 1, line 10 change "in" to - in- -
Column 3, line 39 change "form" to -from- Signed and Sealed this Fourteenth Day of July, 1992

Attest:

DOUGLAS B. COMER

*Attesting Officer*  *Acting Commissioner of Patents and Trademarks*